(12) United States Patent
Karazivan et al.

(10) Patent No.: US 11,045,295 B2
(45) Date of Patent: Jun. 29, 2021

(54) THREE-DIMENSIONAL PRINTING SYSTEM AND METHODS OF USE (71) Applicant: DENTSPLY SIRONA INC., York, PA (US)

(72) Inventors: Naim Karazivan, Repentigny (CA); Hui Lu, Magnolia, DE (US); Thomas Ertl, Ranstadt (DE)

(73) Assignee: DENTSPLY SIRONA Inc., York, PA (US)

( * ) Notice: Subject to any disclaimer, the term of this patent is extended or adjusted under 35 U.S.C. 154(b) by 932 days.

(21) Appl. No.: 15/352,274

(22) Filed: Nov. 15, 2016

(65) Prior Publication Data

US 2017/0071712 A1  Mar. 16, 2017

Related U.S. Application Data

(62) Division of application No. 14/587,090, filed on Dec. 31, 2014, now Pat. No. 9,675,435.
(Continued)

(51) Int. Cl.
*A61C 13/15* (2006.01)
*G01N 21/64* (2006.01)
(Continued)

(52) U.S. Cl.
CPC .......... *A61C 19/003* (2013.01); *A61B 5/0071* (2013.01); *A61B 5/0088* (2013.01);
(Continued)

(58) Field of Classification Search
CPC ..... A61C 13/0019; A61C 19/003; A61C 7/14; A61C 7/146; A61C 7/16; A61C 5/30;
(Continued)

(56) References Cited

U.S. PATENT DOCUMENTS 4,957,441 A   9/1990 Bryan
5,451,785 A   9/1995 Faris
(Continued)

FOREIGN PATENT DOCUMENTS

EP   0375161 A2   6/1990
EP   1240878 A1   9/2002
(Continued)

OTHER PUBLICATIONS

Alexander Stepuk, Dirk Mohn, Robert N. Grass, Matthias Zehnder, Karl W. Kramer, Fabienne Pelle, Alban Ferrier and Wendelin J. Stark, "Use of NIR light and upconversion phosphors in light-curable polymers," SciVerse ScienceDirect (www.sciencedirect.com), p. 304-3011, Nov. 22, 2011.
(Continued)

*Primary Examiner* — Jeffrey M Wollschlager
(74) *Attorney, Agent, or Firm* — Dentsply Sirona Inc.

(57) ABSTRACT

A three-dimensional printing system including a feed source of uncured filled resin material, a print head configured to apply discrete layers of a composition including upconversion phosphors, and a radiation source configured to irradiate layers of uncured filled resin material and deposited layers of the composition is provided. A method of three dimensionally printing a dental article is also provided.

16 Claims, 7 Drawing Sheets

Related U.S. Application Data (60) Provisional application No. 61/922,162, filed on Dec. 31, 2013.

(51) Int. Cl.

| | | |
|---|---|---|
| *C09D 5/22* | (2006.01) | |
| *A61C 13/00* | (2006.01) | |
| *A61B 5/00* | (2006.01) | |
| *B33Y 10/00* | (2015.01) | |
| *B33Y 80/00* | (2015.01) | |
| *A61C 5/30* | (2017.01) | |
| *B33Y 30/00* | (2015.01) | |
| *A61C 5/70* | (2017.01) | |
| *A61C 5/77* | (2017.01) | |
| *B29C 64/129* | (2017.01) | |
| *A61C 13/09* | (2006.01) | |
| *A61K 6/25* | (2020.01) | |
| *A61K 6/30* | (2020.01) | |
| *A61K 6/40* | (2020.01) | |
| *A61K 6/70* | (2020.01) | |
| *A61K 6/78* | (2020.01) | |
| *A61K 6/822* | (2020.01) | |
| *A61K 6/824* | (2020.01) | |
| *A61K 6/838* | (2020.01) | |
| *A61K 6/887* | (2020.01) | |
| *A61C 7/14* | (2006.01) | |
| *A61C 7/16* | (2006.01) | |
| *B29L 31/00* | (2006.01) | |

(52) U.S. Cl.
CPC .............. *A61C 5/30* (2017.02); *A61C 5/70* (2017.02); *A61C 5/77* (2017.02); *A61C 7/14* (2013.01); *A61C 7/146* (2013.01); *A61C 7/16* (2013.01); *A61C 13/0019* (2013.01); *A61C 13/09* (2013.01); *A61K 6/25* (2020.01); *A61K 6/30* (2020.01); *A61K 6/40* (2020.01); *A61K 6/70* (2020.01); *A61K 6/78* (2020.01); *A61K 6/822* (2020.01); *A61K 6/824* (2020.01); *A61K 6/838* (2020.01); *A61K 6/887* (2020.01); *B29C 64/129* (2017.08); *B33Y 10/00* (2014.12); *B33Y 30/00* (2014.12); *B33Y 80/00* (2014.12); *C09D 5/22* (2013.01); *G01N 21/64* (2013.01); *A61B 2562/164* (2013.01); *B29L 2031/7536* (2013.01); *G01N 21/6428* (2013.01); *G01N 2021/6439* (2013.01); *G01N 2021/6495* (2013.01)

(58) Field of Classification Search
CPC .. A61C 5/70; A61C 5/77; A61C 13/09; A61K 6/25; A61K 6/30; A61K 6/40; A61K 6/70; A61K 6/78; A61K 6/822; A61K 6/824; A61K 6/838; A61K 6/887; B29C 64/129; C09D 5/22; B33Y 10/00; B33Y 80/00; B33Y 30/00; B29L 2031/7536; G01N 21/6428; G01N 2021/6439; G01N 2021/6495; G01N 21/64; A61B 5/0088; A61B 5/0071; A61B 2562/164
See application file for complete search history.

(56) References Cited

U.S. PATENT DOCUMENTS

| | | |
|---|---|---|
| 6,008,264 A | 12/1999 | Ostler et al. |
| 6,730,715 B2 | 5/2004 | Jia |
| 6,783,810 B2 | 8/2004 | Jin et al. |
| 7,314,610 B2 | 1/2008 | Loveridge |
| 2002/0167100 A1* | 11/2002 | Moszner ............ A61C 13/0004 264/16 |
| 2004/0196538 A1 | 10/2004 | Burgener, II et al. |
| 2005/0202363 A1 | 9/2005 | Osterwalder |
| 2006/0193779 A1 | 8/2006 | Loveridge |
| 2006/0194172 A1 | 8/2006 | Loveridge |
| 2006/0194895 A1 | 8/2006 | Loveridge et al. |
| 2006/0223032 A1 | 10/2006 | Fried et al. |
| 2007/0238056 A1 | 10/2007 | Baumann et al. |
| 2008/0057000 A1 | 3/2008 | Loveridge |
| 2009/0079993 A1 | 3/2009 | Yatagai et al. |
| 2009/0081461 A1 | 3/2009 | Yi et al. |
| 2009/0130449 A1 | 5/2009 | El-Siblani |
| 2010/0297206 A1 | 11/2010 | Kim et al. |
| 2011/0200971 A1 | 8/2011 | Kalgutkar et al. |
| 2012/0064477 A1 | 3/2012 | Schmitt |
| 2012/0280144 A1 | 11/2012 | Guilfoyle et al. |
| 2013/0134309 A1 | 5/2013 | Rapaport |
| 2013/0190192 A1 | 7/2013 | Lowe |
| 2013/0323685 A1 | 12/2013 | Ostler et al. |
| 2014/0110872 A1 | 4/2014 | Levy et al. |

FOREIGN PATENT DOCUMENTS

| | | |
|---|---|---|
| EP | 2052693 A1 | 4/2009 |
| JP | 2002186632 A | 7/2002 |
| WO | 9733922 A1 | 9/1997 |
| WO | 2005105412 A1 | 11/2005 |
| WO | 2012070053 A1 | 5/2012 |
| WO | 2013184647 A1 | 12/2013 |

OTHER PUBLICATIONS

Li Li, Cao Xue-Qin, Zhang You and Guo Chang-Xin, "Synthesis and upconversion luminescence of Lu2O3:Yb3+, Tm3+ nanocrystals," Science Direct (www.sciencedirect.com), p. 373-379, Sep. 22, 2011.

Elixir William Barrera, Maria Cinta Pujol, Francesc Diaz, Soo Bong Choi, Fabian Rotermund, Kyung Ho Park, Mun Seok Jeong and Concepcion Cascales, "Emission properties of hydrothermal Yb3+, Er3+ and Yb3+, Tm3+-codoped Lu2O3 nanorods: upconversion, cathodoluminescence and assessment of waveguith behavior," Nanotechnology 22 (2011) 075205, p. 1-15, Jan. 14, 2011.

Q. Huang, et al., "Synthesis and Characterization of Highly Efficient Near-Infrared Upconversion Sc3+/Er3+Yb3+ Tridoped NaYF4", J. Phys. Chem. C 2010, 114, pp. 4719-4724.

M. UO, E, Kudo et al., "Preparation and Properties of Dental Composite Resin Cured Under Near Infrared Irradiation", Journal of Photopolymer Science and Technology, vol. 5, No. 5 (2009), pp. 551-554.

Chunxia Li, Zewei Quan, Piaoping Yang, Jun Yang, Hongzhou Lian and Jun Lin, "Shape controllable synthesis and upconversion properties of NaYbF4/NaYbF4:Er3+ and YbF3/YbF3:Er3+ microstructures," Journal of Materials Chemistry (www.rsc.org/materials), p. 1353-1361, Jan. 9, 2008.

\* cited by examiner

THREE-DIMENSIONAL PRINTING SYSTEM AND METHODS OF USE

RELATED APPLICATIONS

This application is a divisional application of U.S. Non-Provisional patent application Ser. No. 14/587,090 entitled "DENTAL COMPOSITIONS CONTAINING UPCONVERSION PHOSPHORS AND METHODS OF USE", filed Dec. 31, 2014, which claims the benefit of and priority to U.S. Application No. 61/922,162 filed Dec. 31, 2013, both of which are hereby incorporated by reference in its entirety.

FIELD

The present invention relates to dental materials that employ upconversion phosphors and applications for using those materials. These dental materials include coatings for use with curable resins for selective curing of materials as well as in films and other diagnostic materials.

BACKGROUND

Dental cements play a vital role in dentistry and resin-based dental cements are becoming widely used. Cements in dentistry are typically used to attach a dental fabrication/prosthetic (e.g. brackets, crowns, bridges, etc.) to dental structures (e.g. teeth) by placing a thin layer of cement at the tooth-fabrication interface. In most cases, excess cement is present and flows from the interface and needs to be removed. Removing excess cement is typically done before any curing or before complete curing of the cement. This step of excess cement removal is often repetitive and/or difficult to perform because the excess cement is usually present in a confined area. As a result, cement removal is often not done in a very accurate fashion and/or takes a lot of time for a dental professional to remove. For example, during the placement of a dental crown or bridge, excess cement should be removed from the margins of the restoration before the cement is completely cured; accordingly this step must be done quickly and can induce some stress (and thus increase the likelihood of error) for the clinician that must acquit this task precisely and quickly.

These and other drawbacks are present in the art.

Exemplary embodiments are directed to dental materials and applications that employ upconversion phosphors useful in overcoming various existing drawbacks as more fully described herein.

SUMMARY

A luminescent coating is disclosed that is used to dimensionally control the curing of a photo curable agent placed in close contact with the coating. This coating is applied at the interface of structures (or directly on a curable material in case of 3D printing) at the location where the bonding material is required to be cured. This luminescent coating irradiates from its structure the curing radiations necessary to photopolymerize the resin, typically in the blue or UV spectrum. This radiation is emitted only when one form of first radiation is irradiated on its structure; typically a red or infrared radiation source is used as the first radiation.

The coating is calibrated by using the desired concentration of active luminescent material in order to emit sufficient radiation to cure a pre-determined thickness of bonding material during a predetermined irradiation time with the first exciting radiation. This type of coating is particularly useful in dentistry for cemented structures (orthodontic brackets, fixed prosthesis like bridges, crowns, inlays or onlays or interproximal film application) and is useful for fast 3D printing techniques of highly particles filled resins and for other industrial uses requiring spatial control of the curing of the resin.

Additionally, this type of coating may be used in diagnostic for visualizing in visible spectrum the infrared invisible radiations. For example this is useful for the transillumination with penetrating infrared to examine the inside structures (like caries) in a confined space like the dental interproximal surface of teeth—in this case additional long lasting luminescence substrate for prolongation of the visible illumination may be used.

In one embodiment, a luminescent coating comprises a binder and upconversion phosphors wherein the upconversion phosphors emit radiation at a predetermined wavelength matching an initiator activation wavelength of a photoinitiator in a corresponding dental cement when the upconversion phosphors are irradiated with radiation having a wavelength of at least 780 nm. In some embodiments, the coating consists of just the upconversion phosphors or just the upconversion phosphors and a resin binder. In some embodiments, the upconversion phosphors comprise an inorganic host lattice doped with a rare earth ion.

The coating may be applied as a thin coating in various dental applications.

In one embodiment, a method of attaching a dental article to the surface of a tooth comprises providing the dental article to be attached to the surface of the tooth, applying a coating comprising upconversion phosphors to a surface of the dental article configured to face toward the surface of the tooth, applying to the surface of the tooth a dental cement composition comprising a polymerizable resin and a photoinitiator, the dental cement composition substantially free of upconversion phosphors, placing the dental article on the surface of the tooth such that the coating comprising upconversion phosphors is adjacent the dental cement composition, irradiating the coating comprising upconversion phosphors with a radiation source that emits radiation at a pre-determined fixed wavelength in a range of the electromagnetic spectrum that causes the upconversion phosphors to emit radiation at an activation wavelength of the dental cement composition photoinitiator such that the dental cement composition cures in a region adjacent the coating and removing remaining uncured dental cement composition outside the dental article from the tooth. In some embodiments, the dental article is an orthodontic bracket, which may be ceramic, metal, or of another material. In other embodiments, the dental article is a dental prosthetic, such as a crown, and may be all ceramic or built on a metal base.

In yet another embodiment, a method of three dimensionally printing a dental article comprises providing a first layer comprising an uncured resin material, a photoinitiator, and in the range of about 50% to 90% by weight inert filler particles, depositing, via a print head, a first discrete layer of a composition comprising upconversion phosphors to a predetermined surface region of the first layer of uncured resin material, providing a second layer of the uncured resin material overlying the first layer of uncured resin material and the deposited layer that comprises the upconversion phosphors, depositing, via a print head, a second discrete layer of the composition comprising upconversion phosphors to a predetermined surface region of the second layer of uncured resin material, providing a third layer of the uncured resin material overlying the second layer of uncured resin material and the second deposited layer that comprises the upconversion phosphors, irradiating the layers of uncured resin material and deposited layers comprising upconversion phosphors with a wavelength that causes to the particles to luminesce at a wavelength corresponding to an activation wavelength of the photoinitiator in the uncured resin material and thereby curing the resin material in a region adjacent the particles to form a cured resin mass and separating remaining uncured resin material from the cured resin mass. The layers of the composition comprising upconversion phosphors are deposited to the predetermined surface regions of the uncured resin material in a pattern corresponding to a predetermined form of the dental article.

In still another embodiment, a three-dimensional printing system comprises feed source of uncured filled resin material comprising a polymerizable resin, photoinitiator, and inert filler, a print head configured to apply discrete layers of a composition comprising upconversion phosphors to predetermined surface regions of incrementally stacked layers of the uncured filler resin material in a pattern corresponding to a predetermined form of a dental article and a radiation source configured to irradiate layers of uncured filled resin material and deposited layers of the composition comprising upconversion phosphors with a wavelength that causes to the particles to luminesce at a wavelength corresponding to an activation wavelength of the photoinitiator in the uncured filled resin material thereby curing the resin material in a region adjacent the particles to form a cured resin mass.

Exemplary embodiments also related to the use of upconversion coatings in diagnostic applications. In one embodiment, a method of diagnosing an optical inhomogeneity of a volume scattering object such as a tooth comprises providing a substrate coated with upconversion phosphors, adapting the substrate to a surface of a volume scattering object to be diagnosed, trans-illluminating the volume scattering object with radiation such that the upconversion phosphors emit radiation in a different portion of the electronic magnetic spectrum having a shorter wavelength than the incident radiation to thereby expose the film and determining the presence of or lack of optical inhomogeneity based on a spatially varying level of exposure of the film.

According to still another embodiment, a method of diagnosing an optical inhomogeneity of a volume scattering object comprises providing a substrate coated with afterglow phosphorous particles, adapting the substrate to a surface of a volume scattering object to be diagnosed, and trans-illuminating the volume scattering object with green or blue radiation such that the afterglow phosphorous particles emit radiation for a longer time duration sufficient to remove the substrate from the diagnosed object and place it in a reader to be digitized.

In yet another embodiment, a dental tool includes a substrate comprising a transparent flexible film or metallic foil, the substrate having applied thereon a coating comprising upconversion phosphors.

Numerous features and advantages will be apparent from the following more detailed description of exemplary embodiments, which taken in conjunction with the accompanying drawings, illustrate principles of the invention.

BRIEF DESCRIPTION OF THE DRAWINGS

Where like parts appear in more than one drawing, it has been attempted to use like reference numerals for clarity.

DETAILED DESCRIPTION OF EXEMPLARY EMBODIMENTS

Exemplary embodiments are directed to compositions containing upconversion phosphors, also referred to herein as upconverting luminescent particles or crystals, and the use of such particles in conjunction with curable resins for applications in which a spatially controlled curing of the resin is desired such as in confined areas as well as the use of such particles in diagnostic applications. As used herein, the term resin encompasses any material that can be light cured.

In one embodiment, the invention relates to a composition, generally applied as a thin coating, comprising upconversion (e.g. second-harmonic generation (SHG), third-harmonic generation (THG), anti-stokes) phosphor particles. These particles (often in a crystalline form) emit lower wavelength (higher energy) luminescence radiation upon excitation using higher wavelength (lower energy) radiation. This nonlinear process is achieved by using upconversion phosphors to absorb multiple higher wavelength photons per single emitted lower wavelength photons. Thus, as used herein, upconversion refers to materials that, when exposed to a radiation source having a particular primary wavelength or range of wavelengths (e.g., red, infrared or near-infrared), in turn emit radiation having a wavelength shorter than that of the incident radiation (e.g., blue visible or ultra-violet).

Of particular interest in compositions in accordance with exemplary embodiments are upconversion phosphors that emit radiation at a wavelength in the UV-A or visible violet or blue range (320 nm to 495 nm) when irradiated with radiation having a longer wavelength, and more particularly when irradiated with near-infrared radiation having a wavelength in the range of about 780 nm to 1064 nm.

Rare earth (RE) doped upconversion phosphors are generally composed of an inorganic host lattice (commonly containing trivalent rare earth ions such as $Y^{3+}$, $Sc^{3+}$, $Lu^{3+}$, for example), doped with trivalent lanthanide (Ln) series ions (such as $Yb^{3+}$, $Tm^{3+}$, $Er^{3+}$, $Ho^{3+}$, $Pr^{3+}$, for example), although any other suitable upconversion phosphors in the form of oxides, halides, oxysulfides, and oxyfluorides may be used that exhibit photon emission with a wavelength complementary to the light-curing or dual-curing (light curing and dark-curing) properties of the cement (or more specifically of the photoinitiator) to be employed therewith. The invention is not limited to RE doped, inorganic upconversion phosphors and any other materials having the upconversion luminescent properties may also be employed, such as metal—organic complex and lanthanide-transition metal hybrid complexes having upconversion luminescent properties, for example.

Coatings in accordance with exemplary embodiments comprising upconversion phosphors are highly desirable in a variety of applications, particularly those in which spatial control of the curing of the resin is important. For example, in some embodiments, the excitation radiation is in the vicinity of the near infrared spectrum with an emitting luminescence in the vicinity of the blue or violet spectrum. Such a luminescent coating allows the cementation of artificial or natural (e.g. tooth) structures to bond the structures together without having to worry about excess cement curing in an undesired area, as the curing can be accomplished neatly at the desired location.

Coating Composition.

The coatings in accordance with exemplary embodiments may be as simple as the upconverting phosphor particles themselves, but typically include a binder and more typically include a curable binder of some type. In currently preferred embodiments, upconversion coatings for use in most dental applications comprise a mixture of upconverting crystal particles and resin base, in which the ratio of particles to resin ranges from 1 to 95% by mass. The specific concentration of particles in any particular application may vary, but is selected such that the concentration is sufficient to cure at least a portion of the full thickness of an adjacent layer of cement (typically having a thickness of 25-500 microns) using a predetermined level and exposure time of initial exciting radiation, which in some embodiments may be at least 25% by weight or at least about 50% by weight, for example. It is preferred to have an upconverting crystal concentration higher than those used in composite applications using upconversion crystals such as described in U.S. Pub. 2013/0323685, which is hereby incorporated by reference in its entirety.

Suitable upconversion phosphors for use with exemplary embodiments of the present invention include those that employ lanthanide fluorides (such as $NaLnF_4$ (Ln=Yb, Y, Lu, Gd, Tm, Er, Ho, Dy, Eu, Tb, Nd), $LiYF_4$, $LiLuF_4$, $YF_3$, $GdF_3$, $LaF_3$, $Na_5Ln_9F_{32}$ (Ln=Tm, Yb, Lu), etc), oxysulfides (such as $Y_2O_2S$, $Eu_2O_2S$, $La_2O_2S$, $Gd_2O_2S$, etc) or oxides (such as $Lu_2O_3$, $Y_2O_3$, $Er_2O_3$, $Gd_2O_3$, $CeO_2$, $ZrO_2$, etc) hosts, that are doped or co-doped with one or more trivalent rare earth ions (lanthanide series ions plus scandium ($Sc^{3+}$) & yttrium ($Y^{3+}$)), such as ytterbium ($Yb^{3+}$) lutetium ($Lu^{3+}$), thulium ($Tm^{3+}$), terbium ($Tb^{3+}$), erbium ($Er^{3+}$), and praseodymium ($Pr^{3+}$). The lanthanide dopants are optically active centers and frequently include a combination of sensitizers and activators. By facile control of the host lattice (type, phase, size, etc), and dopant ion type, concentration, and sensitizer to activator ratio, the luminescent crystals' absorption and upconversion emission properties can be fine-tuned and optimized.

In co-doped luminescent rare earth crystals with strong upconversion emission in blue light wavelength, such as $NaYF_4$:$Yb^{3+}$/$Tm^{3+}$, $NaYbF_4$:$Yb^{3+}$/$Tm^{3+}$, $NaLuF_4$:$Yb^{3+}$/$Tm^{3+}$, $Lu_2O_3$:$Yb^{3+}$/$Tm^{3+}$, $Y_2O_2S$:$Yb^{3+}$/$Tm^{3+}$, the molar ratio of sensitizer (e.g., $Yb^{3+}$) to activator (e.g. $Tm^{3+}$) may be from 1:1 to 50:1, respectively. The inverse ratios of 50:1 to 1:1, respectively, are also useful. It will be appreciated that a variety of factors, such as host/dopant composition, synthesis method, solvent/chelating agent used, pH, heat treatment, thermodynamic stability, etc., can be used to optimize the size, shape, and phase of the upconversion phosphors for a particular desired application.

Having Yb as part of the matrix that hosts either $Er^{3+}$ or $Tm^{3+}$ may have superior performance to other forms in which other rare earth metals are associated in the matrix, such as the co-doped salt $\beta$-$NaYF_4$:$Yb^{3+}$, $Tm^{3+}$ in which the molar percentages are from 0.01 to 30% respectively and, again the inverse 30 to 0.01% respectively is also useful. For the oxide based host, co-doped crystals such as $Lu_2O_3$:$Yb^{3+}$, $Tm^{3+}$ with similar molar concentrations may also be used to generate intense blue photons.

The coating of upconversion phosphors can be made of a resin and particles that are of comparable thickness to the cement to be employed (e.g., 25 to 250 microns), while in some embodiments the coating can be as thin as a few microns, such as less than 20 microns, less than 15 microns, or in the range of about 5 to 10 microns, particularly when high weight percentages of crystals are employed in the coating. The resin base used in the coating is typically selected to be the same or at least compatible with the resin used in the type of cement to be employed.

In some embodiments, the concentration of crystals may be around 50% by weight, for example, of the resin, which may be useful to provide enough viscosity, but as discussed previously a wide range of concentrations may be used depending upon the type of application.

In some embodiments, the chemical adhesion of the cement used in conjunction with the coating may be enhanced by providing the coating containing an inhibited layer of resin at the coating surface, which may be done, for example, by exposing the coating containing the upconversion phosphors to ambient oxygen during curing. Such inhibited surfaces chemically bond to the resin cement if made with the chemically compatible resin systems. Using such a coating with a same/compatible resin base (as opposed to a non-compatible resin base) may enhance the application of this resin to any conventional dental restoration without any special modification to the surface or the structure.

The resin base of the coating can be any polymerizable monomer and/or oligomer, but is typically one or more (meth)acrylates or other free radically polymerizable compounds. Exemplary polymerizable monomers include, without limitation, mono-, di- or multi-methacrylates and acrylates such as 2,2-bis[4-(2-hydroxy-3-methacryloyloxypropoxy)phenyl] propane (Bis-GMA); 1,6-bis(2-methacryloxyethoxycarbonylamino)-2,4,4-trimethylhexane (UDMA); 2,2-bis[4-(methacryloyloxyethoxy)phenyl] propane (or ethoxylated bisphenol A-dimethacrylate) (EBPADMA); isopropyl methacrylate; triethyleneglycol dimethacrylate (TEGDMA); diethyleneglycol dimethacrylate; tetraethyleneglycol dimethacrylate; 3-(acryloyloxy)-2-hydroxypropyl methacrylate; 1,3-propanediol dimethacrylate; 1,6-hexanediol dimethacrylate (HDDMA); pentaerythritol triacrylate; pentaerythritol tetraacrylate; pentaerythritol tetramethacrylate; and combinations thereof, all by way of example.

In addition to the upconversion phosphors and any resin matrix, coating compositions in accordance with exemplary embodiments may optionally also include inert filler particles. Any inert filler particles that are suitable for use in dental compositions may be employed. Inert fillers can be used to provide the composition with additional desired physical, rheological and optical properties. Exemplary inert filler particles include, but are not limited to, strontium borosilicate, strontium fluoroalumino borosilicate glass, strontium alumino sodium fluoro phosphor-silicate glass, barium borosilicate, barium fluoroalumino borosilicate glass, barium aluminum-borosilicate glass, barium alumino borosilicate, calcium alumino sodium fluoro silicate, lanthanum silicate, lanthanum aluminosilicate, calcium alumino sodium fluoro phosphor silicate, and combinations thereof. Other filler particles include silicon nitrides, titanium dioxide, fumed silica, colloidal silica, quartz, kaolin ceramics, calcium hydroxy apatite, zirconia, and mixtures thereof. If employed, the inert filler is generally provided having a particle size in the range about 0.001 microns to about 50 microns.

Some or all of any inert filler particles, as well as the upconversion crystal particles, can optionally be surface treated prior to incorporation into the composition. Surface treatments, particularly those using silane coupling agents or other compounds may be desirable for the inert filler particles to be more uniformly dispersed in the organic resin matrix and can further improve physical and mechanical properties. Suitable silane coupling agents include 3-methacryloxypropyltrimethoxysilane, 3-acryloxypropyltrimethoxysilane, 3-glycidoxypropyltrimethoxysilane, 3-mercaptopropyltrimethoxysilane, and mixtures thereof.

The coating composition also optionally includes one or more types of a photoinitiator. Any suitable photoinitiator that dissociates to form an initiating species may be employed, although the photoinitiator is preferably effective in the visible light spectrum range, such as those currently employed in other dental restorative applications. The activation wavelength of the photoinitiators may range from about 360 nm to about 520 nm, particularly from about 400 nm to 500 nm, although it will be appreciated that the specific range and peak activation (i.e. absorption) wavelength will depend upon the particular photoinitiator selected. For example, camphorquinone (CQ) absorbs energy preferentially in the visible blue spectrum (in the range of about 420 nm to 500 nm), having a peak absorption at 468 nm.

Exemplary suitable photoinitiators include diketone type initiators such as CQ, derivatives of diketone initiator, and acylphosphine oxide type photoinitiator such as diphenyl (2,4,6-trimethylbenzoyl) phosphine oxide (L-TPO), and combinations thereof. Other diketone type photoinitiator such as 1-phenyl-1,2 propanedione (PPD), and acylphosphine oxide type photoinitiator such as bis(2,4,6-trimethylbenzoyl)-phenylphospohine oxide (Irgacure 819), ethyl 2,4,6-trimethylbenzylphenyl phosphinate (Lucirin LR8893X), may also be used. Any of the foregoing may be used individually or in combination with one another.

Matching Cement with Luminescent Coating.

As already discussed, coatings in accordance with those described can advantageously be used in combination with a dental cement to initiate curing in locations that are difficult to reach or for which spatial curing is otherwise desired. The cement to be used with the luminescent coatings described herein can be any cement, including such as are known to those of ordinary skill in the art and which generally may, without limitation, employ one or more of the resins and/or photoinitiators already discussed with respect to the luminescent coating. It will be appreciated, however, that the bonding of the cement to the luminescent coating is enhanced by using a cement comprising the same base resin (if any) of the coating or one that is compatible therewith. It will further be appreciated that the translucency of the cement (e.g., translucency to initial infrared radiation and/or to secondary emitted blue or UV radiation) used may impact the results. Increasing translucency enhances the depth of cure (e.g. thicker cement), while decreasing translucency is beneficial for reducing the amount of cured cement that exudes out of the interface (radius of illumination at the interface), and thus the specific translucency preferred may vary depending upon application. It will be appreciated that generally, a variation of translucency to the initial radiation has an effect on the depth of cure and a variation of translucency to the secondary, emitted radiation has an effect on the radius of curing around the crystal particle.

It will further be appreciated that the cement should be substantially free of upconversion phosphors, as incorporating such particles may defeat the ability to easily clear away uncured cement after exposure to IR radiation that causes the phosphors to emit the blue light that initiates curing. That is, upconversion phosphors are not usually intentionally introduced into the cement and, if so, are typically in such a small amount as to not initiate curing generally throughout the cement.

In some embodiments, it may not be necessary to cure the whole thickness of the cement. For example, the upconversion coating may be used to generate radiation that initiates curing in the margins of the cement, while final curing may result from another curing mechanism. For example, in the case of stainless steel brackets (as discussed subsequently in more detail), because light cannot transmit through the stainless steel, the initial infrared (or other wavelength depending upon the particular crystals employed) illumination may be used to cure only the peripheral/marginal portions because the light density may not be enough for full cure completely underneath the bracket. After the curing of the cement around the margins, the clinician may remove any excess cement and subsequent to this easy excess removal, use conventional blue curing light or self-curing to finish the curing of the unreached areas (i.e., a blue or UV light that emits a strong band of radiation at the activation wavelength of the photoinitiators, typically from about 360 nm to about 520 nm, particularly from about 400 nm to 500 nm).

Application of Coating.

The precise application of the coating is typically important to prevent curing at undesired locations. The radius of the action of curing around the upconverting particles can also be taken into account when applying the coating on the dental structure; the coating is preferably applied in order to have the curing occurring closest to the margins but not too far inside or outside of the contour of the tooth in order to obtain the maximum smooth biological contouring typically desired in dental restorations. For example, if the radius of curing around the particles is about 100 microns, then the coating is applied at the interface short of 100 microns from the margins, which results in the curing stopping at the margins.

For dental fixtures such as brackets and prosthetics, as well as other articles, application of the coating can be made in the dental laboratory or manufacturing environment during the creation of the dental fabrication. Alternatively, the application can also be made chairside, with the clinician applying the coating on the finished structure prior to installation. The clinician can verify its efficiency by shining the first radiation on the applied coating and examining the secondary radiation. The application is readily accomplished by applying like a conventional dental adhesive, such as using a sprayable coating or any other suitable method of application. As discussed previously, the coating may be made exclusively with luminescent particles without any resin, in which case the cement wets the luminescent particles and incorporates them into its structure on application. Bare upconversion particles are also particularly useful in 3-D printing embodiments, which involves printing the coating as discussed further with respect to those embodiments.

It will be appreciated that in order to increase the ease of application or adhesion of the coating to the structure, or to control the application of the cement, it is possible to include some special texture inside the structure on the inner surface of the dental structures to be cemented, such as micro cavities.

Orthodontic Brackets.

According to one embodiment, coating compositions disclosed herein are used in conjunction with cement to attach orthodontic brackets to the teeth as schematically illustrated in FIGS. 1a-1d.

Figure 1A:
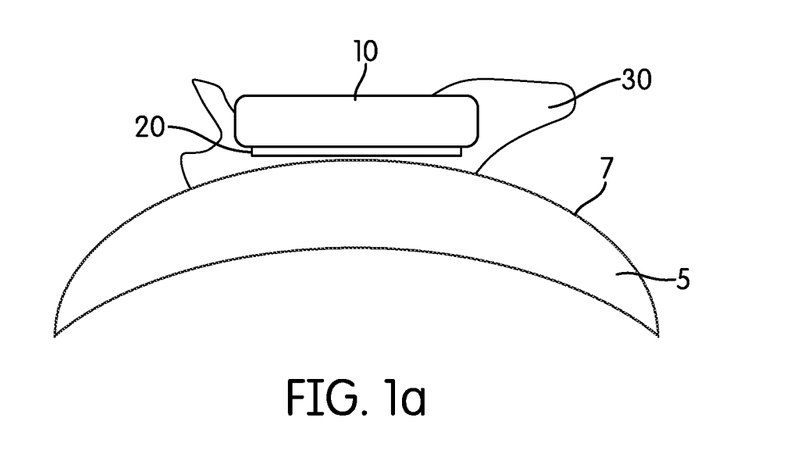
FIGS. 1a through 1d illustrate use of an upconversion phosphor coating in the cementation of orthodontic brackets according to an exemplary embodiment.

FIG. 1a shows a bracket 10 ready to be affixed to the labial surface 7 of a tooth 5. To the surface of the bracket 10 that faces the tooth has been applied a thin layer of the upconversion coating 20 as described herein. It will be appreciated that the coating 20 is typically applied to a very thin thickness as already described (e.g. less than 250 microns) and that the relative thicknesses of this and other items shown in the figures are for ease of illustration and not meant to be to scale. The coated face of the bracket 10 is placed onto the labial surface 7 of the tooth 5 and comes into contact with an uncured dental cement 30 for securing the bracket 10 to the tooth 5, the cement 30 having been applied prior to placement of the bracket 10. As illustrated, the uncured dental cement 30 is typically in a liquid state, with excess cement 30 shown surrounding the bracket 10 as generally occurs during bracket installation, particularly as the bracket 10 displaces some of the cement 30 during placement.

Figure 1B:
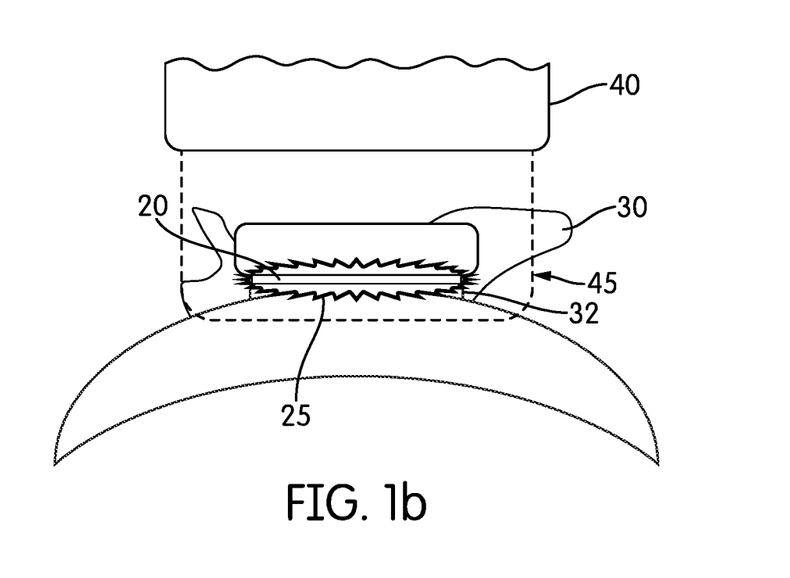
Figure 1C:
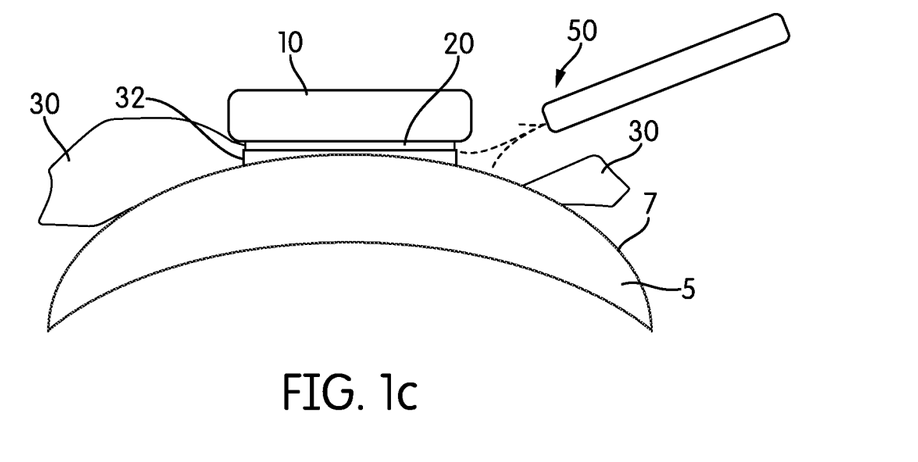
Figure 1D:
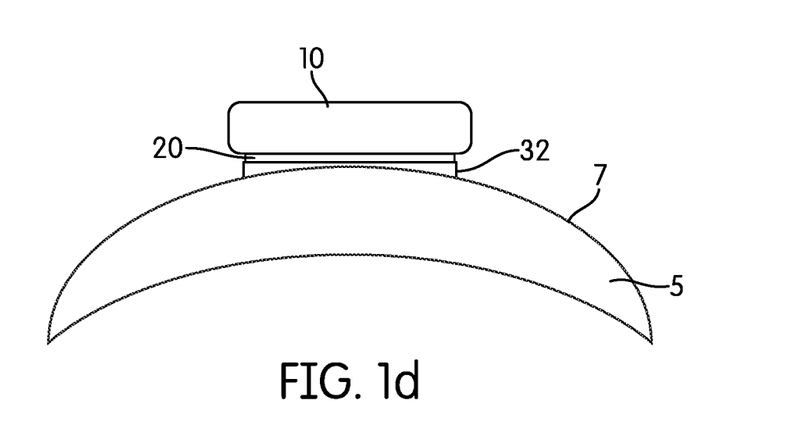

Turning to FIG. 1b, a curing light 40 that emits radiation 45 in the IR band is shined on the tooth 5. The IR radiation 45 does not cause the cement 30 to cure generally because its radiation does not activate photoinitiators within the cement 30, the cement being free of the phosphors. However, the luminescent phosphors in the upconversion coating 20, when stimulated by the IR radiation 45, emit blue light 25 that causes the photoinitiator in the cement 30 to dissociate and thus the cement in the immediate area near the applied coating cures to form a region of cured cement 32. In FIG. 1c, the cement 30 that was not in the vicinity of the applied coating 20 remains in its uncured state and can be easily cleaned away, for example using an air or water blast from an air-water sprayer 50 of a dental hand piece, leaving behind the bracket 10 secured to the tooth 5 by a thin layer of cured cement 32 at the desired locations as shown in FIG. 1d.

In the case of ceramic orthodontic brackets, the upconversion coating can simply be applied on the bracket's tooth-facing surface and irradiating illumination may be made directly through the ceramic bracket because infrared light transmits through the ceramic material as illustrated in FIGS. 1a-1d. In the case of metallic brackets, the coating can be applied in the same fashion, although the infrared radiation (and subsequent cure inducing blue luminescence of the upconversion coating) is used primarily for tacking the bracket in position by curing the cement at the interface periphery (locations that are sufficiently reached by the initial IR radiation), which still allows easy removal of the uncured excess cement as the IR radiation may not penetrate through the metal with sufficient intensity to generate enough blue photons. By curing the peripheral portion, uncured cement to secure the bracket is trapped inside the cured periphery, allowing the mechanical removal of excess cement outside the periphery as shown in FIG. 1c. A conventional blue light source (which generates a larger amount of blue photons compared to that of the upconversion particles) can then be used to more easily cure the surfaces under the metal bracket to finish curing of non-peripheral areas (i.e., those directly behind the bracket where the IR radiation did not reach because of the metal shield), while the excess uncured cement outside the bracket has been removed so that the subsequent use of the blue light doesn't have an undesirable result in curing cement still on the external part of the teeth.

As a result, in some embodiments employing metallic brackets, it may be desirable to coat only the marginal portions of the bracket with the upconversion coating to reduce the amount of crystal used, as any coating applied to more central surfaces would ordinarily not be effective in regions where IR radiation does not reach in sufficient intensity (i.e., not enough photon density).

According to another embodiment, an inhibiting agent is applied to the exposed uncured cement outside the bracket after the luminescent coating has been used to cure the peripheral portions. This allows, for example in the case of metallic brackets, the curing of the peripheral portions of the cement and subsequently inhibiting the uncured resin with an inhibitor, followed by finishing the curing with the conventional blue light method or with another curing mechanism without the need to first remove the uncured cement outside the bracket. Typical polymerization inhibitors for a free radical system may include hydroquinine monomethyl ether (MEHQ), butylated hydroxytoluene (BHT), tertiary butyl hydro quinine (TBHQ), hydroquinone, phenol, and the like. The use of an inhibiting agent permits postponing the removal of excess cement material until after the full curing is completed. Alternatively, when an inhibitor is applied, two radiation sources can be used or a dual wavelength radiation source may be used to emit both the IR and the conventional blue light contemporaneously.

Crown, Bridges and Other Fixed Prostheses.

Figure 2:
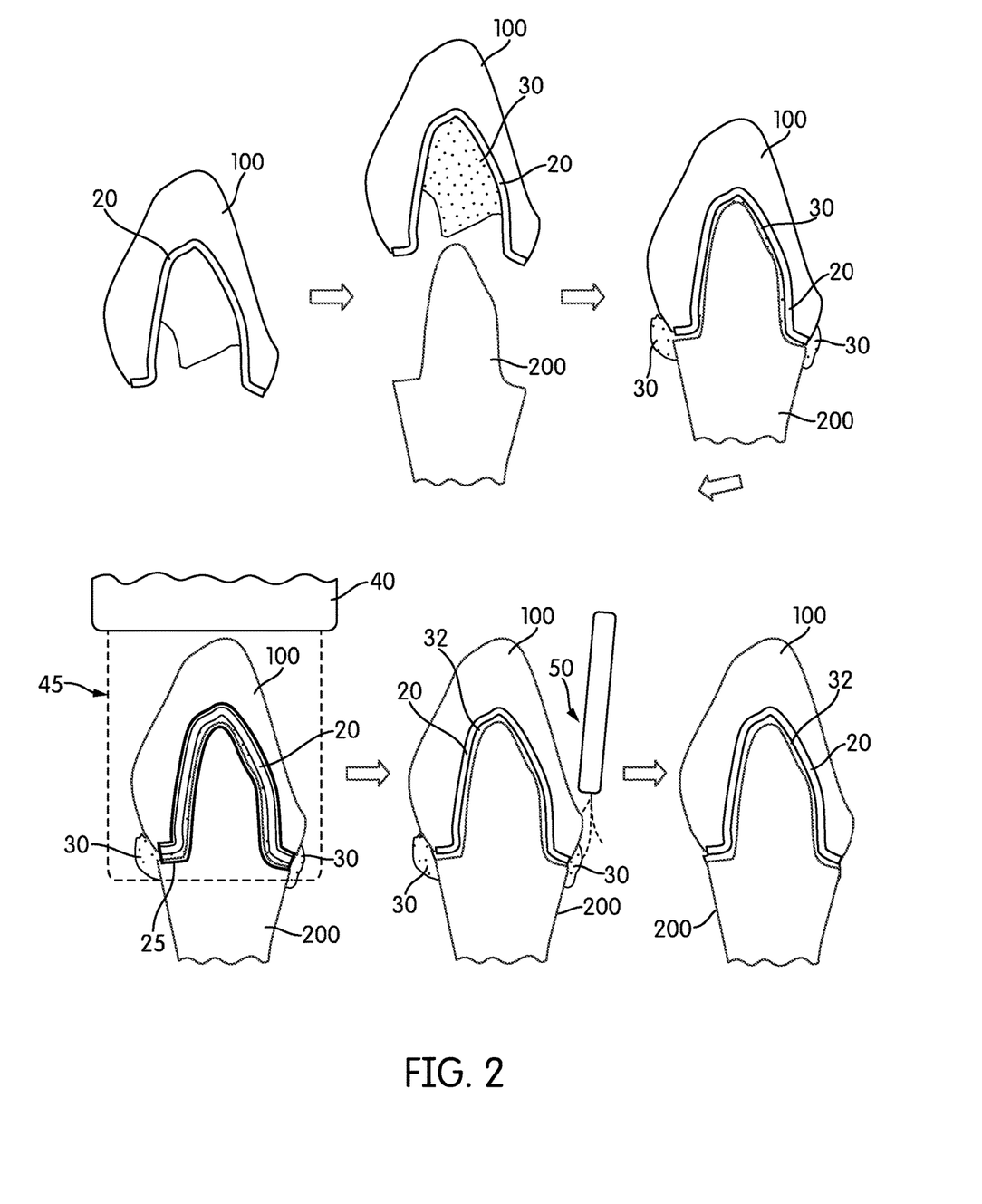
FIG. 2 schematically illustrates the use of an upconversion phosphor coating in a dental crown fabrication according to an exemplary embodiment.
Figure 3:
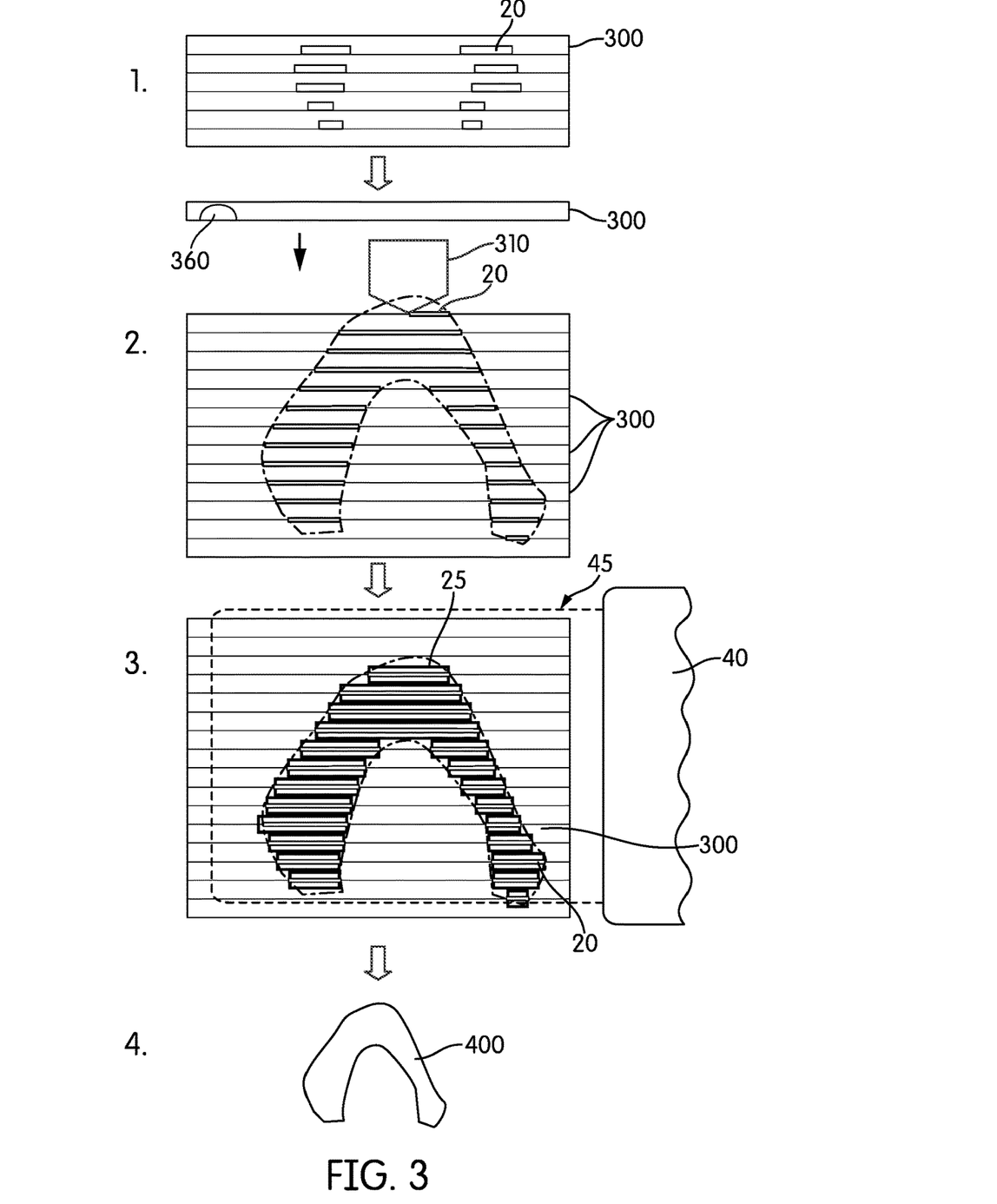
FIG. 3 schematically illustrates the use of an upconversion phosphor coating in 3D printing fabrication of a dental structure in accordance with an exemplary embodiment.

According to other exemplary embodiments, compositions described herein may be used to affix dental prostheses, such as bridges and crowns by way of example, shown schematically in FIG. 2 with respect to a prosthesis 100 illustrated in the context of a crown. In the case of fixed prostheses, the upconversion coating 20 is applied on the internal surface of the prosthesis 100 that will be in contact with the tooth structure 200. Conventional light curable cement 30 is also applied to the internal surface of the prosthesis overlying the upconversion coating 20, upon which the prosthetic 100 is placed by the clinician. This generally results in excess cement 30 oozing from the periphery. In a similar manner to that described with respect to affixing the orthodontic brackets, once the prosthesis 100 has been placed, a curing light 40 that emits infrared light 45 (or other radiation complementary to the excitation spectra of the upconversion phosphors) is used to activate the coating 20, causing the coating 20 to irradiate a blue light 25 (or other radiation complementary to the spectra needed to cause dissociation of the photoinitiator) that results in cured cement 32 at the interface of the prosthesis 100 and tooth structure 200. (It will be appreciated that the boundary of the blue light 25 shown in the figures, such as FIGS. 2 and 3, is for simplicity of illustration and is not meant to represent the exact manner in which the light is emitted).

After curing the cement at the interface, the remaining uncured cement 30 that oozed out of the interface can be removed such as by an air blast or other manner (including cement curing inhibitors) from an air-water sprayer 50, leaving behind the permanently affixed prosthetic 100 as the final result. The remaining uncured cement 30 is easily removed because it remains in its uncured, low viscosity state having not been in proximity with the upconversion coating 20 and thus not exposed to the blue light 25 emitted upon IR excitation of the coating 20, leaving it in the uncured state.

It will be appreciated that in some embodiments, the upconversion phosphors may also or alternatively be incorporated directly into the ceramic powder used to form the restoration and/or its tooth contacting surface. As a result, the upconversion crystals (which can resist high temperatures) may be sintered directly as part of the ceramic structure without having to subsequently apply them as a coating to the finished prosthesis. Alternatively, the coating may be applied directly on the tooth structure by the clinician in a form of a primer, adhesive, or the like.

Application of the coating directly on the tooth surface renders the same result of selective, dimensionally controlled curing of the cement. In some embodiments, the surface of the crown or the dental structure may be sandblasted and/or silanized to increase wettability and increase the creation of retentive microstructures and therefore enhance adhesion with the coating and cement.

Similarly to the case of metallic brackets, for metallic crowns, bridges or other fixed prostheses, the upconversion luminescent coating allows peripheral curing using infrared irradiation. However, also like the case of metallic brackets previously described, after the periphery is cured, excess cement is easily removed and the uncured cement remaining inside the periphery of the prosthesis is cured in another mode, typically using a conventional blue light, self-curing mechanism, or dual-curing mechanism.

3D Printing.

Some 3D printing methods are known for curing layer by layer with a light source irradiating the desired area of the resin, also layer by layer. However, these printers typically use low viscosity resins to allow easy handling of the material when making layers. Printing resins that are highly filled with particles remains challenging in 3D printing, largely because of the challenges associated with controlling the curing area and depth, which can be compromised due to scattering of the filling particles. Controlling paste viscosity with precise delivery is another hurdle faced in 3D printing of highly filled resin. Furthermore, in typical 3D printing using a photo curable resin, the processing time is slow because it requires substantial amounts of time between each layer (3-5 seconds/layer).

Exemplary embodiments of the invention overcome these challenges by using the luminescent upconversion coatings described herein in the coating that is printed over layers of highly filled light curable resin resulting in very precise, very fast printing.

Turning to FIG. 3, which schematically illustrates a 3D printing process, layers 300 of filled uncured resin material are incrementally stacked with a thin layer of the luminescent coating 20 (preferably consisting of only the upconversion phosphors in printing embodiments) applied over each resin layer 300 using a print head 350 of a jet printer or any suitable other deposition method. Depositing the coating 20 of luminescent particles between resin layers 300 enables precise control of curing in the region where the luminescent particles are placed.

The shape of the desired structure, which in the case of dental structures may be a bridge, crown or other structure, is defined by the area of the coating 20 printed over each successive filled resin layer 300. When the stack of filled resin layers 300 is completed and the printing of the coating completed to define the desired structure, the entire stack is irradiated with an IR light or other radiation source 40 to expose the stack to IR (or other) radiation 45. As described with respect to prior embodiments, this causes the emission of blue light 25 in the vicinity of the coating 20 of printed luminescent particles, causing the resin layers 300 to cure at those locations to form a cured resin mass 400 in the desired three-dimensional shape, after which the remaining uncured resin 300 can be removed, leaving the cured resin mass 400.

Composition of the filled resin layers may be the same as that used in forming a dental composite. For example, the filled resin layer may be in the range of about 15 to 25 percent by weight polymerizable resin (monomer and/or oligomers), typically about 17 to about 23% by weight. The polymerizable organic resin may be any polymerizable monomer and/or oligomer, but is typically one or more (meth)acrylates or other free radically polymerizable compounds. Exemplary polymerizable monomers include those described previously for use as the resin binder in the luminescent coating composition, including mono-, di- or multi-methacrylates and acrylates such as Bis-GMA, UDMA, EBPADMA, TEGDMA, HDDMA, pentaerythritol triacrylate, pentaerythritol tetraacrylate, pentaerythritol tetramethacrylate, and combinations thereof, all by way of example.

In certain embodiments, the polymerizable monomer of the filler resin layer is a combination of a high molecular weight component (such as Bis-GMA 513 g/mol and/or UDMA 471 g/mol, for example) and a low molecular weight component (such as TEGDMA 286 g/mol and/or HDDMA 254 g/mol, for example). In one embodiment, the polymerizable monomer is present at about 14 to about 18% by weight of the high molecular weight component and about 3 to about 5% by weight of the low molecular weight component in the overall filled resin layer.

The filled resin layer includes inert filler particles and any inert filler particles that are suitable for use in dental compositions may be employed. The inert fillers provide desired physical properties such as increased mechanical strength, modulus, hardness, wear resistance, reduced thermal expansion, and polymerization volumetric shrinkage. Exemplary inert filler particles include, but are not limited to, strontium borosilicate, strontium fluoroalumino borosilicate glass, strontium alumino sodium fluoro phosphor-silicate glass, barium borosilicate, barium fluoroalumino borosilicate glass, barium aluminum-borosilicate glass, barium alumino borosilicate, calcium alumino sodium fluoro silicate, lanthanum silicate, lanthanum aluminosilicate, calcium alumino sodium fluoro phosphor silicate, and combinations thereof. Other filler particles include silicon nitrides, titanium dioxide, fumed silica, colloidal silica, quartz, kaolin ceramics, calcium hydroxy apatite, zirconia, and mixtures thereof.

Examples of fumed silica include OX-50 from DeGussa AG (having an average particle size of 40 nm), Aerosil R-972 from DeGussa AG (having an average particle size of 16 nm), Aerosil 9200 from DeGussa AG (having an average particle size of 20 nm), other Aerosil fumed silica might include Aerosil 90, Aerosil 150, Aerosil 200, Aerosil 300, Aerosil 380, Aerosil R711, Aerosil R7200, and Aerosil R8200, and Cab-O-Sil M5, Cab-O-Sil TS-720, Cab-O-Sil TS-610 from Cabot Corp.

The inert filler has a particle size in the range about 0.001 microns to about 50 microns.

Some or all of the inert filler particles can optionally be surface treated prior to incorporation into the composition used of the filled resin layer. Surface treatments, particularly those using silane coupling agents or other compounds may be desirable for the inert filler particles to be more uniformly dispersed in the organic resin matrix, and also improve physical and mechanical properties. Suitable silane coupling agents include 3-methacryloxypropyltrimethoxysilane, 3-acryloxypropyltrimethoxysilane, 3-glycidoxypropyltrimethoxysilane, 3-mercaptopropyltrimethoxysilane, and mixtures thereof.

The inert filler particles form the bulk of the filled resin layers and may be present in amounts of from about 50% to about 90% by weight, such as from about 60% by weight to about 80% by weight percent, or from about 70% to about 75% by weight of the filled resin layer. In one embodiment, the inert filler particles are present at about 56% by weight, about 57%, about 58%, about 59%, about 60%, about 61%, about 62%, about 63%, about 64%, about 65%, about 66%, about 67%, about 68%, about 69%, about 70%, about 71%, about 72%, about 73%, about 74%, about 75%, about 76%, about 77%, about 78%, about 79%, about 80%, about 81%, about 82%, about 83%, about 84%, or about 85% by weight, or any range there between.

In one embodiment, the filler can comprise a mixture of a micron-sized radiopaque filler such as barium alumino fluoro borosilicate glass (BAFG, having an average particle size of about 1 micron) with nanofiller particles, such as fumed silica such as OX-50 from Degussa AG (having an average particle size of about 40 nm). In one embodiment, the concentration of micron-size glass particles ranges from about 70 weight percent to about 80 weight percent of the filled resin layer, and the nanofiller sized inert filler particles can range from about 1 weight percent to about 10 weight percent of the filled resin layer.

As described with respect to the coatings in other embodiments previously described, the filled resin layer is substantially free of upconversion phosphors.

Printing an upconversion coating of even a few microns thickness can be used to cure a 25 micron thick filled resin layer and in some cases up to 250 microns thick, depending on the conversion rate and the exposure time. The filled resin layers may be delivered as a preformed ribbon 350 (shown in FIG. 4b) of a defined thickness of the composition. The resin layers can optionally include different colors, one in contact to another and with different colors and/or opacities. The resin layer can also include hard structures 360 to act as mechanical stoppers when layers are pressed one over another, in order to control the layer thickness. These stoppers can be made of already cured filled resin material formed by curing some portion of the resin filled layers in defined, known locations. These hard stoppers are designed to be aligned one over the other in order to allow controlled compression of layers to a predetermined thickness (i.e., the thickness of the hard stopper). Within the same layers, different areas of different colors and opacities may be included in contact with each other, using a computer guided technology to arrange the placement of the layers in order to match the desired colors at the desired location.

The radius of curing can be variable for the same particles depending on the geographical location in the volume of the assembled layers 300 because the light density is different in different locations inside the layer stack. Variables include attenuation of radiation with penetration inside the structure and the proximity of the photoinitiator to the emitted photons from the upconversion process.

The density of the applied upconversion coating can be adjusted on a layer by layer basis, analogous to a conventional printing process in which lesser densities of black ink coverage are employed to create different shades of gray. In conjunction with complementary print software used in exemplary embodiments directed to 3-D printing, the level of transmission needed in any one layer is calculated and the application density of the upconversion coating is applied upon the amount of initial radiation expected (this is again related to the time and intensity of initial radiation reached at each geographical location inside the volume of stacked layers). For example, in a thick block of one hundred resin layers, the upconversion coating in the middle of the formed block of layers (where less initial radiation can penetrate) is applied more densely than coatings applied at locations closer to the light source.

Printing in this fashion can result in constructions being formed extremely quickly when compared with conventional 3D resin printing, as waiting time between each layer is eliminated, while printing with an inkjet-like technology using the upconversion coating results in extremely fast and precise application. The complete construction and curing of a structure of around 1 cm×1 cm×1 cm is accomplished in 2 minutes or less.

In some embodiments, particularly to compensate for shrinkage, it may be desirable to expose the structure to infrared irradiation after every layer or every few layers, not only at the end of the stacking process, so that curing of the structure is carried out contemporaneously with the structure's formation.

Figure 4A:
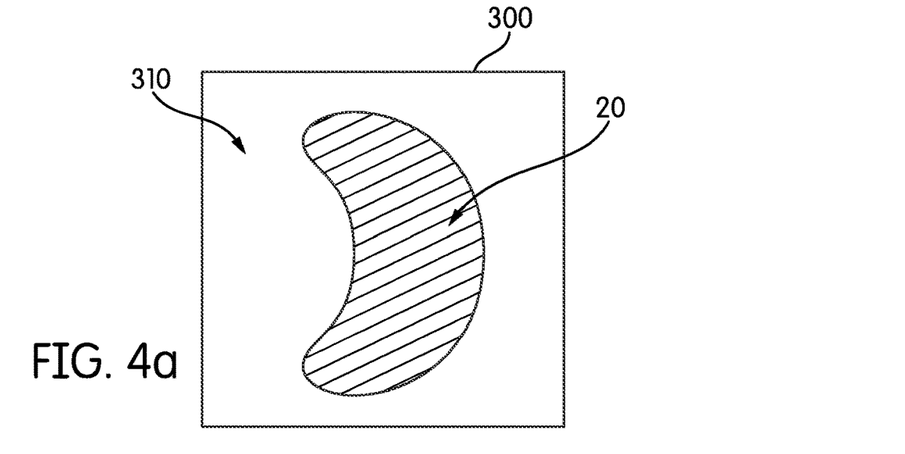
FIGS. 4a through 4c illustrate options for application of the upconversion phosphor coating in 3D printing fabrication accordance with exemplary embodiments.

The schematic illustrated in FIG. 3 is with respect to an embodiment in which the coating 20 of luminescent particles is applied, as shown in FIG. 4a, on regions of the surface 310 of the filled resin layer 300 corresponding to the dental restoration to be formed, with the surface 310 left uncoated on those areas which are to be left uncured and removed from the cured dental mass 400 after curing.

Figure 4B:
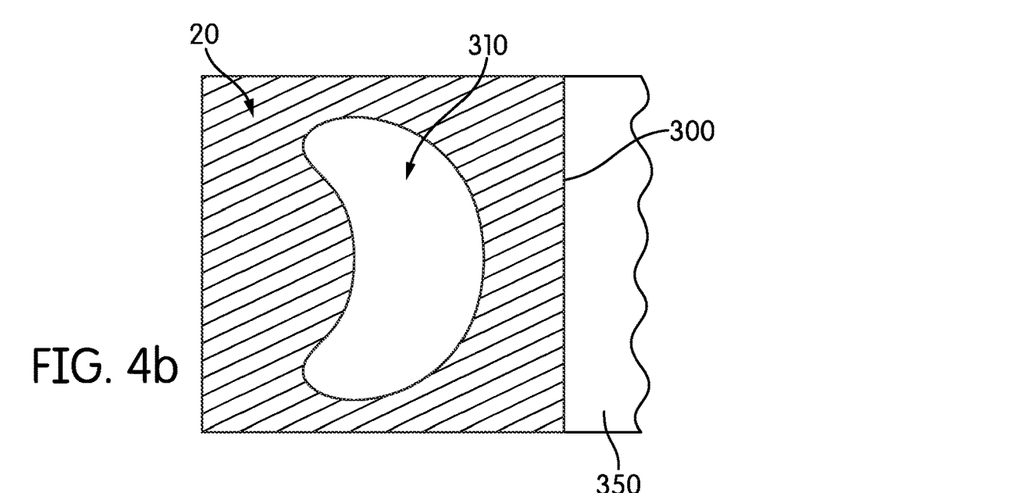
Figure 4C:
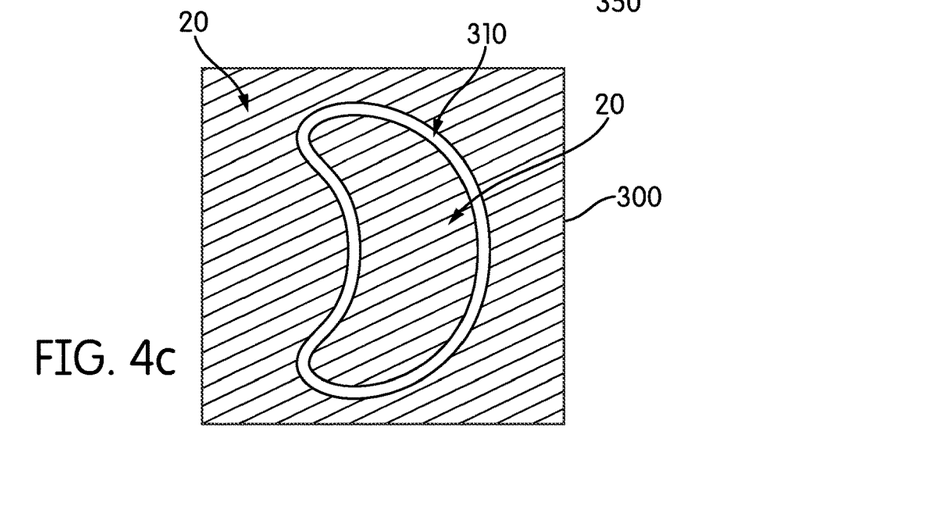

In some embodiments, as shown in FIG. 4c, in order to minimize the time necessary to remove the uncured filled resin after the layering and curing is complete, it may be desirable to arrange the curing to cure a large amount of the remaining layer material surrounding the desired 3D dental fabrication. Thus, in some embodiments most of the surface of each resin layer is printed with upconversion coating 20 with a small gap of exposed surface 310 of the uncured resin layer 300 left which approximates an outline of the structure for each layer and on separation lines. As a result, two cured resin masses are formed as both the undesired surrounding 3D structure (the material surrounding the desired 3D fabrication) and the desired 3D fabrication are cured. The interface between the desired and the undesired structure remains uncured along with separation lines within the undesired structure. The undesired structure is divided in multiple volumes separated by uncured resin interfaces in order to ease the removal of the undesired resin (this eases the removal of undesired resin when undercuts are present).

In this manner, larger blocks of the resin can be more quickly and easily removed from the desired dental structure. Thus, the outside undesired resin is removed like a nutshell to reveal the inside "nut," here the desired 3D fabrication 400. Put another way, the upconversion coating is applied in a manner similar to creating a segmented nut shell around the printed 3D dental structure. After the curing is performed, the undesired blocks are removed leaving the desired structure with only a small layer of uncured material over it.

In either case, secondary operations, including shaping of the dental restoration, may be conducted. In some embodiments, some portion of the remaining uncured resin may still remain and the secondary shaping operations may include smoothing uncured resin over the created structure and curing using a conventional light to render a smoother surface. Vibrating the uncured filled resin or chemically dissolving the uncured filled resin (using alcohol for example) may also be used to result in the desired smooth surface. Alternatively, the structure may be cleaned using a solvent bath.

In yet another embodiment (FIG. 4b), only the outer surface of the 3D fabrication volume is printed with upconversion crystals; that is, the coating 20 of luminescent particles is printed on regions of the resin surface 310 only in areas which are not intended to be part of the final dental structure. Thus, subsequent curing with an IR light results in curing of only the external surface of the 3D dental structure, with the inside left uncured. This results in a cured resin mass in the form of a shell that encapsulates the uncured resin in the form of the dental restoration. The shell can be removed as previously described to reveal the remaining uncured dental restoration. This uncured resin is cured in a second step with blue light using a conventional light curing device.

Curing only the shell may be desirable in some cases to further aid in contouring the surfaces of the finished restoration. In these cases, the shell is cured and removed, revealing the restoration in a still uncured state. As a result, final adjustments to shape and contour can be made while the restoration remains uncured, followed by curing the structure using, for example, a conventional blue light. This may be useful for better esthetics of the final restoration.

Such an encapsulation approach also allows having the restoration done with less upconversion particles used in the process (which saves cost) and may result in better esthetics. The deposition of a coating 20 of upconversion particles over composite resin layers 300 may in some cases result in visible, undesirable structures. Applying composite layers one over the other directly, without upconversion crystals in between layers within the article itself, may result in better esthetic results. In other words, the blending of the particles and the composite may in some circumstances result in visible striations inside the 3D dental structure and therefore it may be preferable in some embodiments to do layering without upconversion particles and cure these encapsulated layers inside this hard shell in a later stage using a different method like a conventional blue curing light.

In some embodiments, this encapsulation method may be used only in desired locations of the volume of the 3D structure (where the final esthetic is more important and/or more apparent, or when particles can be saved if not mechanically jeopardized by this type of encapsulation process). This encapsulation may be used also to cure the outer undesired structures. This may result in the minimization of the amount of upconversion particles used, which can increase flexibility of the outer undesired structures to ease removal and enable the recuperation of the composite by pressing and squeezing out the encapsulated composite inside the undesired structures.

In some embodiments, the encapsulation may be accomplished by the negative of FIG. 4c (i.e., in which only the gap portion is printed with the coating), so that the uncured shell is removed in the conventional fashion, while uncured resin material interior to the dental structure is thereafter cured using a conventional blue curing light.

In yet another embodiment, the resin filled layers may have upconversion particles disseminated directly throughout, being formed of a composition such as described in U.S. Pub. No. 2013/0323685, already incorporated by reference. In this embodiment, infrared power is focalized in a small area that results in a precision curing of the specific area that may be more precise than conducting photo-curing with blue or UV light. Because the upconversion crystals require multiple photons to generate the secondary luminescence, the optical system is designed to have a sufficient concentration of initial radiation in a limited micrometric area and therefore to obtain a similar result to the coating approach without having to print anything on the surface of the layers.

In this embodiment, the upconversion generated photons originate from the inside of the material and not from an external source that has to penetrate from without, decreasing any excessive scattering inside the resin that may result in a larger than desired block of cured resin and providing an additional advantage in the level of control. This embodiment may result in better blending of layers but can also exhibit less bonding between the layers because uncured and cured layers are placed together without an inhibited interface. This embodiment may be used along with the encapsulation approach to maximize the physical characteristics of the 3D dental fabrication (minimize the bonding between layers of uncured with cured layers).

Diagnostic Applications.

A structure consisting of volume scattering material (e.g. ceramic, composite resin, laminates or dental tooth material) can be illuminated in a well accessible area and the light is scattered within the object. Any inhomogeneity changes the scattering pattern and can be detected from outside of the light scattering object. Especially if the inhomogeneity is close to the outside border of the object, imaging is possible by observing the light intensity distribution directly at the object surface. In this case, for example, a crack in a ceramic structure or a delamination of laminates creates a shadow by hindering the photon propagation by a refraction index inhomogeneity. In case of caries of teeth, an erosion of the surface also creates an area with changed refraction index and changed optical properties, (absorption and scattering coefficient and g-factor), which causes differences in the light propagation visible from outside of the volume scattering material.

Observation of these light intensity changes may be difficult, if the inhomogeneity occurs in an area not directly visible by a camera. Such areas include, for example, a tiny spatial confinement in a tool—e.g. a drilling hole with a high aspect ratio (deep and small), a thin slit in a tool, or interproximally between teeth. In such a case, special fiber optic image guides are an expensive option which is prone to fracture.

According to still another embodiment of the invention, the upconversion coatings described herein are used in the formation of a structure useful for diagnostic purposes, and in particular for the otherwise difficult job of diagnosing interproximal caries and fractures. Exemplary embodiments solve this problem with the use of a luminescent material in a shape that fits in the small space available for visualization. This can be a tiny cylinder or bars for inspection of drill holes or rectangular openings or a band like structure fitting into small slits or between teeth.

Figure 5A:
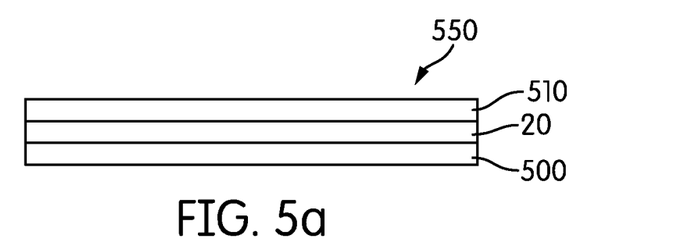
FIGS. 5a through 5c illustrate diagnostic devices containing an upconversion phosphor coating in accordance with exemplary embodiments.
Figure 5B:
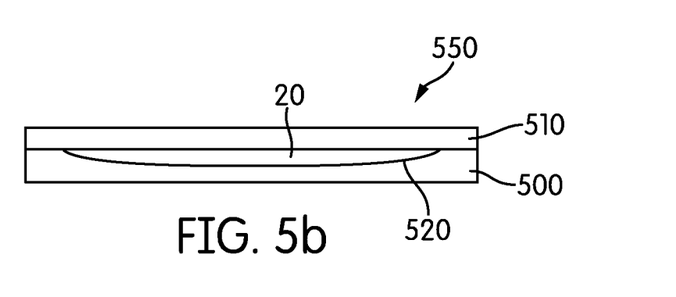
Figure 5C:
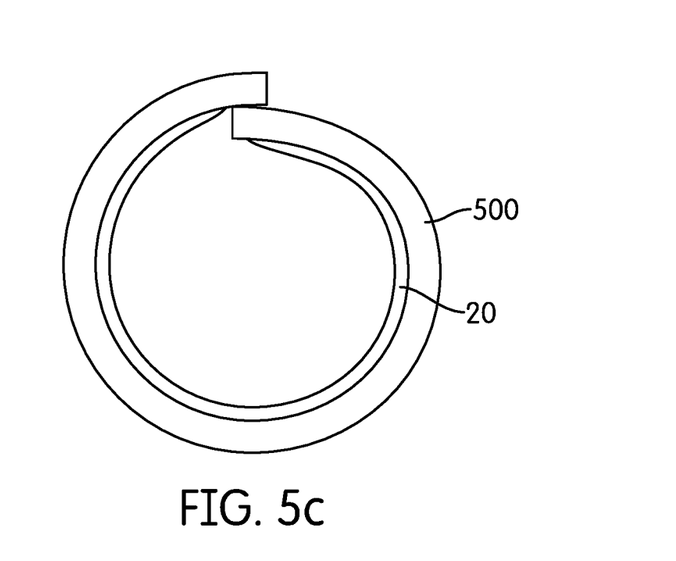

As illustrated in FIGS. 5a-5c, a diagnostic device 550 comprises a substrate 500 containing a coating 20 comprising luminescent particles as previously described, which are able to maintain luminescence for a period of several seconds to minutes. The luminescent particles can be illuminated by a wavelength shorter than the emitted light or in case the luminescent particles can maintain the luminescence for several seconds or minutes and are capable of up-conversion even with a longer wavelength. Long lasting luminescence/phosphorescence particles are added to the upconversion luminescent particles, if the up-conversion particles have a too short luminescence lifetime.

In this embodiment, the device 550 is typically formed in the shape of a matrix band or a wide floss that can be inserted interproximally and then adapted by pressing on the interproximal tooth surface. Alternatively, the device 550 can be rolled into a small cylinder (FIG. 5c) for insertion within a tooth for diagnosis, for example, to check for fractures.

The substrate 500 structure contains a coating of luminescent particles and when illuminating the tooth with IR or red or visible radiation, the film is exposed, with more radiation where the interproximal decay is not present. In case of decay of enamel, the scattering coefficient is higher than in sound enamel, thus more light is scattered in all directions thus less light remains to illuminate the substrate 500. In case of decay in dentin, additionally the absorption coefficient is higher (brown color of dentin caries). This also reduces the light illuminating the substrate structure 500. In case of a fracture in a volume scattering material a non-homogeneous light intensity distribution is generated by the refraction index difference between the crack and the surrounding material. After the crack (seen from the illumination side) less light is available due to more reflection at the refraction index inhomogeneity. The film is therefore exposed with more radiation when no decay or crack is present; secondary illumination is created proportionally to this first radiation and therefore creating a gradient mapping on the surface of the upconversion coating. A typical interproximal caries or fracture will create a darker area on the film and the clinician can determine the presence of caries when a darker area is present on the film—the darker and the larger the area, the more significant is the decay. A quality engineer or other technician can determine from the intensity distribution the severity of a structural inhomogeneity e.g. a crack or delamination.

In some embodiments, long-lasting luminescent particles, such as certain upconversion phosphors with prolonged decay time, and certain afterglow phosphors having persistent luminescence are added to the upconversion luminescent particles to prolong this blue/UV secondary radiation and allow the luminescence to last during the removal time. Exemplary such after-glow phosphors include, without limitation, particles such as $Eu^{2+}$ doped $SrAl_2O_4$, $Eu^{2+}$ doped $Sr_4Al_{14}O_{25}$, $Ce^{3+}$ doped $BaAl_2O_4$, $Ce^{3+}$ doped $CaAl_2O_4$, $Dy^{3+}$ doped $SrAl_2O_4$, $Dy^{3+}$ doped $SrMgSi_2O_6$, alkali earth metal silicates, ZnS, and calcium sulfide. A camera or a digitizer may be included to capture low level radiation incoming from the film and digitally enhance the contrast and render an image on a display screen. Using upconversion particles excited by red or infrared gives the advantage of higher penetration in highly scattering materials such as dental structures and more profound information for the clinician, engineer or other technician to evaluate. Choosing shorter wavelength increases the number of scattering events and therefore will be more sensitive to scattering related information.

The additional luminescent particles may be added to the coating in order to prolong the effect of the blue light emission, e.g. from a conventional dental curing light. These additional phosphorescent particles may be sensitive to blue-uv emission and generate a residual light for a prolonged amount of time. A film made only with regular long lasting particles excited in the blue spectrum may also be used along with a simple blue light (dental curing light)—while this would not have the advantage of high penetration, it does have the advantage of not requiring upconversion particles and therefore making the product simpler to manufacture.

Combining both illuminations, first with red, NIR or IR radiation along with up-conversion and as second illumination by green/blue light allows the storage of both images simultaneously on the same substrate 500. For example, NIR to up-conversion with up-conversion particles on substrate 500 followed by blue radiation to excite of long lasting luminescence with a first wavelength of a phosphorous substance A. While the second image can result from green or blue light illumination that results in direct excitation of long lasting luminescence with a second wavelength of a phosphorous substance B.

Substrate 500 then emits both the first and second wavelengths over a longer time. Filters for the two wavelengths can be employed in a reader equipped, e.g., with a CCD or CMOS sensor array or line, allows capture of both images simultaneously (e.g. adapted Bayer pattern on the sensor) or with two sensors with either filter of the first or second wavelength in front of the sensor or within two sequential frames, while the filter is switched from the first to second wavelength between the frames.

As a result, two images can be generated on the substrate 500 which allows differentiating features on the tooth surface adjacent to the substrate from those deeper inside the tooth by generating a first image on the substrate by trans-illuminating with the infrared or red radiation and a second image trans-illuminating with the or blue or green light which stimulates another phosphor composition emitting another wavelength different from the wavelength emitted by illumination with red or infrared light.

In some embodiments, the substrate 500 may be a transparent flexible film with a coating 20 that includes the upconversion phosphors and a binder. Alternatively, it may be desirable to include only the phosphors and/or other luminescent particles without a binder, in which case the device may further include a second transparent flexible film 510 on an opposite surface of the coating 20 as the substrate 500 to maintain the coating 20 in place. In some cases, the perimeter of the films may be left uncoated to form a periphery that can be sealed in some manner, such as heat sealing or an adhesive, for example. The flexible plastic films and the coating may all be of a few microns thick typically in the range of about 20 to about 200 microns, preferably in the range of about 25 to about 75 microns. As result, the overall thickness still easily permits interproximal insertion between the contact point while still achieving highly intimate contact and contouring with the interproximal surface to be examined.

Alternatively, the substrate 500 may be a metallic matrix on which the luminescent coating 20 is applied. In this case of a metallic carrier as the substrate 500, a window or a recess 520 in the substrate band where the coating 20 of luminescent particles are placed is preferred to keep the lowest thickness possible to allow a thinner profile and the best insertion in the contact points. It will be appreciated that a thin plastic film 510 may still be used overlying the metallic substrate to keep the coating 20 in place.

Figure 6:
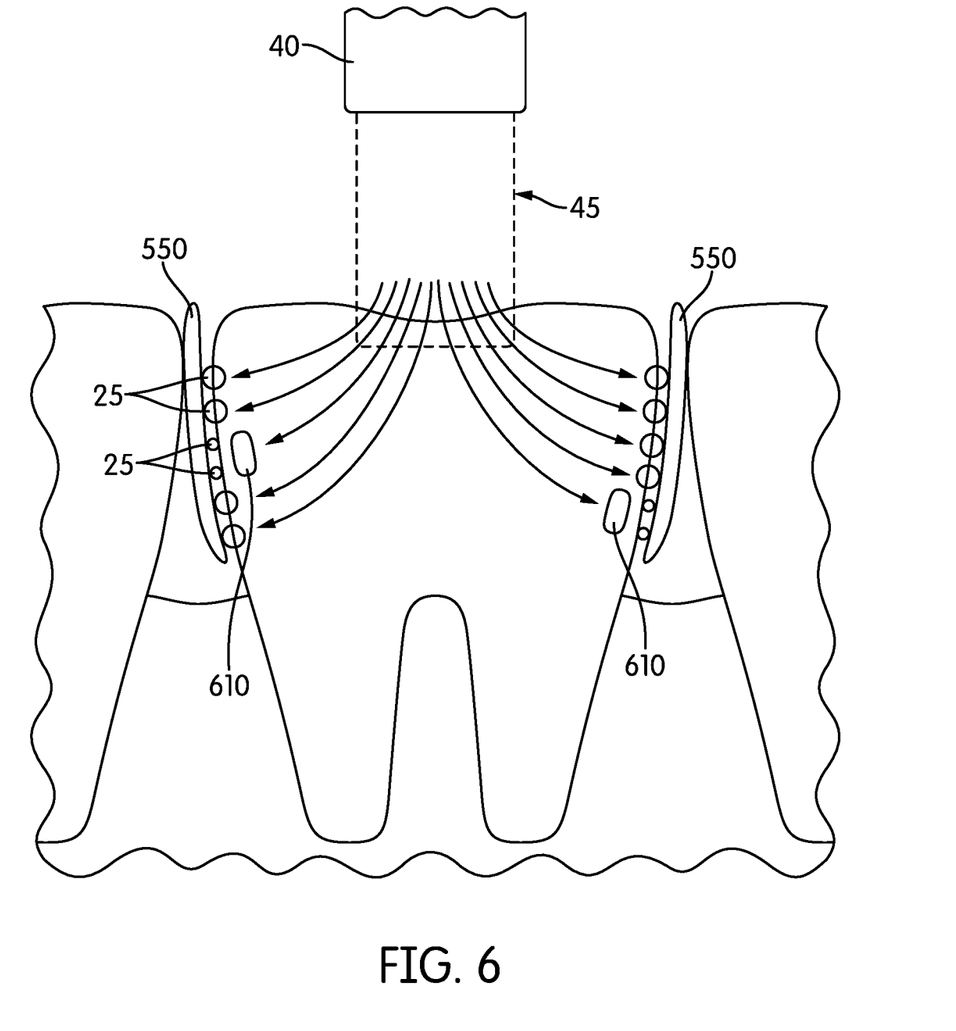
FIG. 6 illustrates the use of an upconversion phosphor coating for interproximal detection of dental caries using a fabrication in accordance with yet another exemplary embodiment.

FIG. 6 schematically illustrates the principles described with respect to the interproximal detection, in which the diagnostic device 550 is inserted interproximally between two teeth, including the tooth to be diagnosed. A radiation source 40 emits radiation 45 that scatters upon entry into the tooth. Radiation that passes out the sides of the tooth does so less through a region containing a carie 610. As a result, photon emission 25 with a shorter wavelength than the irradiated wavelength from the upconversion phosphors in the coating 20 is less intense on regions of the film corresponding to the caries 610 than those regions without caries. After irradiation, the device 550 can be withdrawn from the tooth and a diagnosis made based on the relative illumination of the film, which can be photographed to preserve the mapping observed or digitized with a reader.

Interproximal Coating.

In another embodiment, similar to the caries diagnostic film described above, this same interproximal film including upconversion particles may be used to cure a resin placed in the interproximal area. This may be used to coat the interproximal area and prevent further progress of interproximal caries. The upconversion particles can be placed in a fashion that delimitates the area where the curing of the resin needs to occur and prevent the curing where not desirable (too cervical and too labial, buccal or occlusal). This control of curing allows the precise delimitation of the interproximal coating and therefore a better contouring, softer edges and thus resulting in better biocompatibility and much easier excess removal.

An exemplary embodiment includes having the upconversion particles included in the plastic material and the resin placed between two layers of ultra-thin flexible plastic sheets of a few micrometers that can easily be inserted in any interproximal contact. The resin is carried between the two layers of plastic in the interproximal space and once the films assembly is in contact with the interproximal surface the resin is released by stretching and partial rupturing of one of the two films to release the resin directly onto the surface. The rupture occurs on a pre-punctured line on one of the two films—the one in contact with the tooth surface. The other film has upconversion particles placed in an oval-like shape that delimitates the area where the resin needs to be cured. Once ruptured, the un-ruptured film is conformed on the tooth surface in order to apply a coating of an homogenous thickness. While keeping the film in position in contact with the interproximal surface, the IR radiation is shined on the area allowing the curing of photo curable resin in the vicinity of the upconversion particles inside the film. The films are removed after the curing, leaving the cured and the uncured resin. The resin in this interproximal coating embodiment may be filled in order to ensure a desired thickness of film while applying contouring force over the surface prior to curing.

While the foregoing specification illustrates and describes exemplary embodiments, it will be understood by those skilled in the art that various changes may be made and equivalents may be substituted for elements thereof without departing from the scope of the invention. In addition, many modifications may be made to adapt a particular situation or material including dopants to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A method of three dimensionally printing a dental article comprising:
   providing a first layer of uncured resin material comprising an uncured resin, a photoinitiator, and in the range of about 50% to 90% by weight inert filler particles;
   depositing, via a print head, a first discrete layer of a composition comprising upconversion phosphors to a predetermined surface region of the first layer of uncured resin material;
   providing a second layer of the uncured resin material overlying the first layer of uncured resin material and the deposited layer that comprises the upconversion phosphors;
   depositing, via a print head, a second discrete layer of the composition comprising upconversion phosphors to a predetermined surface region of the second layer of uncured resin material;
   providing a third layer of the uncured resin material overlying the second layer of uncured resin material and the second deposited layer that comprises the upconversion phosphors;
   irradiating the layers of uncured resin material and deposited layers comprising upconversion phosphors with a wavelength that causes the upconversion phosphors to luminesce at a wavelength corresponding to an activation wavelength of the photoinitiator in the uncured resin material and thereby curing the resin material in a region adjacent the upconversion phosphors to form a cured resin mass; and
   separating remaining uncured resin material from the cured resin mass,
   wherein the layers of the composition comprising upconversion phosphors are deposited to the predetermined surface regions of the uncured resin material in a pattern corresponding to a predetermined form of the dental article.

2. The method of claim 1, wherein the layers of upconversion phosphors are deposited on surface regions of the uncured resin layers corresponding to the dental article such that the cured resin mass is in the form of the dental article.

3. The method of claim 2, further comprising conducting secondary shaping operations on the dental article.

4. The method of claim 1, wherein the layers of upconversion phosphors are deposited on surface regions of the uncured resin layers corresponding to a shell portion surrounding the dental article.

5. The method of claim 4, wherein the step of separating comprises removing the cured resin mass as the shell portion such that the remaining uncured resin material is in the form of the dental article and thereafter curing the remaining uncured resin material in the form of the dental article.

6. The method of claim 1, wherein the layers of upconversion phosphors are deposited both on a surface region of the uncured resin layer corresponding to the dental article and a surface region of the uncured resin layer corresponding to a shell portion surrounding the dental article the two surface regions separated by a gap portion of the uncured resin layer surface on which upconversion phosphors are not deposited such the step of irradiating results in a first cured resin mass in the form of the dental article and a second cured resin mass in the form of a shell at least partially surrounding the dental article.

7. The method of claim 6, wherein the step of separating comprises removing the shell at least partially surrounding the dental article and thereafter removing remaining uncured resin mass from a surface of the dental article.

8. The method of claim 7 further comprising conducting secondary shaping operations on the dental article.

9. The method of claim 1, wherein the provided layers of uncured resin material have a thickness in the range of about 25 microns to about 250 microns.

10. The method of claim 1, wherein at least one of the provided layers of uncured resin material has a mechanical stopper to control layer thickness.

11. The method of claim 1, wherein the provided layers of uncured resin material are provided from a continuous ribbon of material.

12. The method of claim 1 wherein a coating density of the upconversion phosphors of the first deposited layer is different from a coating density of the upconversion phosphors of the second deposited layer.

13. The method of claim 1, wherein the upconversion phosphors of the composition of the deposited first discrete layer comprise an inorganic host lattice doped with a rare earth ion.

14. The method of claim 13, wherein the inorganic host is selected from the group consisting of lanthanide fluorides, oxysulfides, fluorides, oxide hosts, a ytterbium fluoride salt, a yttrium fluoride salt, lutetium oxide, and yttrium oxide.

15. The method of claim 13 wherein the inorganic host lattice is doped or co-doped with one or more trivalent rare earth ions.

16. The method of claim 15, wherein the trivalent rare earth ions are selected from the group consisting of ytterbium ($Yb^{3+}$), lutetium ($Lu^{3+}$), thulium ($Tm^{3+}$), terbium ($Tb^{3+}$), erbium ($Er^{3+}$), praseodymium ($Pr^{3+}$), scandium ($Sc^{3+}$), yttrium ($Y^{3+}$) and combinations thereof.

* * * * *